(12) United States Patent
Helgerson

(10) Patent No.: US 6,296,633 B1
(45) Date of Patent: Oct. 2, 2001

(54) MEDICAL DEVICE TUBING ASSEMBLY AND METHOD OF MAKING THE SAME

(75) Inventor: Jeffrey A. Helgerson, Minneapolis, MN (US)

(73) Assignee: Schneider (USA) Inc., Plymouth, MN (US)

( * ) Notice: Subject to any disclaimer, the term of this patent is extended or adjusted under 35 U.S.C. 154(b) by 0 days.

(21) Appl. No.: 09/005,426

(22) Filed: Jan. 9, 1998

(51) Int. Cl.$^7$ ................................................ A61B 17/00
(52) U.S. Cl. .................................................. 606/1; 606/108
(58) Field of Search ........................... 606/158, 226, 606/228, 1, 108; 604/282; 285/382.2; 623/1.11, 1.12

(56) References Cited

U.S. PATENT DOCUMENTS

| | | | |
|---|---|---|---|
| 1,961,453 | * | 6/1934 | Quarnstrom ............................ 137/75 |
| 2,504,625 | * | 4/1950 | Barnhart et al. ...................... 285/111 |
| 4,140,125 | * | 2/1979 | Smith .................................... 606/158 |
| 4,592,372 | * | 6/1986 | Beranek ................................ 128/786 |
| 4,660,559 | * | 4/1987 | McGregor et al. ................... 606/226 |
| 4,806,182 | | 2/1989 | Rydell et al. ......................... 156/211 |
| 5,026,377 | | 6/1991 | Burton et al. ......................... 606/108 |
| 5,452,921 | * | 9/1995 | Hyatt et al. ............................. 285/23 |
| 5,484,444 | | 1/1996 | Braunschweiler et al. .......... 606/108 |
| 5,591,172 | | 1/1997 | Bachmann et al. .................. 606/108 |
| 5,613,973 | * | 3/1997 | Jackson et al. ...................... 606/113 |
| 5,628,755 | | 5/1997 | Heller et al. ......................... 606/108 |
| 5,662,703 | | 9/1997 | Yurek et al. .............................. 623/1 |
| 5,759,185 | * | 6/1998 | Grinberg ................................. 606/80 |
| 5,846,184 | * | 12/1998 | Corriveau et al. .................... 600/160 |
| 5,858,556 | * | 1/1999 | Eckert et al. ......................... 428/586 |
| 6,036,697 | * | 3/2000 | DiCaprio .............................. 606/108 |

OTHER PUBLICATIONS

*Swaging Machine Service Manual* from Torrington Swager and Vaill End Forming Machinery Inc., cover page and pp. 1–36, unknown date of publication.

\* cited by examiner

*Primary Examiner*—Michael H. Thaler
(74) *Attorney, Agent, or Firm*—Todd P. Messal

(57) ABSTRACT

The invention relates generally to a swaged medical device tubing assembly such as a stent delivery system handle or catheter system and making the same.

1 Claim, 4 Drawing Sheets

MEDICAL DEVICE TUBING ASSEMBLY AND METHOD OF MAKING THE SAME

BACKGROUND OF THE INVENTION

The invention relates to a ductile metal tube and tubing assembly and a method of making the same, more particularly, a medical device assembly or stent delivery system handle assembly.

A stent delivery device is used in various medical procedures to deliver a prosthesis or treatment to a body vessel. Such devices require superior mechanical characteristics because they are often pushed a significant distance from the body access site to the treatment site.

Various stent delivery devices are known and disclosed in U.S. Pat. Nos. 5,026,377; 5,484,444; 5,591,172; 5,628,755; and 5,662,703.

All references cited herein, including the foregoing, are incorporated herein in their entireties for all purposes.

SUMMARY OF THE INVENTION

The invention relates generally to a swaged ductile metal tubing over a plastic or polymer tubing and a method of making a medical device assembly.

The invention advantageously connects a ductile metal such as stainless steel in the form of a tube with a second member without using adhesives. For additional strength, the proximal end of the second member is mechanically rolled over forming a rollover member adjacent the end of the ductile metal tube. These procedures mechanically lock the assembly together. The handle assembly also serves as a structural portion which the valve body slides over during stent deployment and reconstrainment. A hub may be disposed over the proximal end of the assembly over the rollover member and ductile metal tube.

Generally, a stainless steel tube is bonded to the interior tube using a cyanoacrylate adhesive. In the present invention, swaging the stainless steel tube to the interior tube advantageously eliminates the need for an adhesive bond or adhesive curing with UV light and therefore reduces manufacturing time. The swaged assembly provides generally superior visual inspection as compared to an adhesively bonded tube assembly that has been through, for example, a UV cure cycle.

Swaging is a process of reducing a ductile metal tube to a smaller predetermined diameter. Properly shaped dies rotate around the work and strike blows at suitable intervals and overlapping areas to produce a generally smooth surface and smaller diameter. Reducing the outer diameter causes a similar reduction in the inside diameter in the swaged tube. Swaging equipment is available from Torrington Swager and Vaill End Forming Machinery Inc. in Waterbury, Conn.

In the present invention, a stainless steel tube is placed over the plastic or polymer interior tube. Preferably, a mandrel is inserted into the plastic tube beneath the area where swaging occurs to support the tubing during the impact forces on the outside of the tube. After swaging, the inside diameter of the interior tube is generally not reduced in diameter due to a properly sized mandrel in the interior tube during the swaging process. Generally, a mandrel about 0.002 inches in diameter less than the inside diameter of the interior tube is desired during swaging. Use of the mandrel is necessary to prevent the lumen from reducing in size or the interior tube being damaged during the swaging process. With proper die selection, it is unlikely that a mandrel would be captured by the assembly. Generally, swaging does not displace tubing material sufficiently to prevent removal of the mandrel.

The assembly is fed into the swaging machine and the outer ductile metal tube is deformed to a predetermined smaller diameter over approximately a one inch length. After swaging, a portion of the length of the metal tube is reduced in diameter. A generally corresponding reduction in the inside diameter of the stainless steel tube will cause the inside surface of the metal tube to contact and become embedded in the plastic or polymer interior tube and form a mechanical bond. With properly sized swaging dies, the metal material is formed down onto the interior tubing and makes intimate contact therewith.

A Rockwell hardness of 85B is the maximum preferred hardness for carbon steels to be used for swaging. Austenitic stainless steels such as the AISI 304 series are preferred for swaging. Other metals with similar ductile properties may also be used.

The preferred die design is a standard single taper. Other designs such as double taper, double extension, or single extension may also be used. Die size is determined by the amount of material that must be moved to form the swaged bond between the metal tube and the polymer tube. Generally, a maximum diameter reduction of 0.002 inches to 0.004 inches in the metal tube is preferred in order to prevent excessive cracking or folding of the material.

The interior tube is preferably made of polyetheretherketone such as a PEEK material which is a high temperature, semi-crystalline material with generally high temperature and strength properties. During the swaging process, the swaged steel tube embeds into the surface of the interior tube. PEEK material lends itself to swaging as it does not spring back appreciably. PEEK material is commercially available and has a flexural modulus ranging from about 440,000 psi to about 2,400,000 psi. PELLETHANE material is a thermoplastic polyurethane elastomer with a Shore A hardness ranging from about 55 to 95 and a Shore D hardness ranging from about 45 to 85. Other plastics, polymers and metal tubes are envisioned to be interior members disposed in the ductile metal tube and a component of the swaged assembly in the present invention.

In addition to the swaging process, a portion of the plastic tubing extending proximal of the metal tube may be rolled over to substantially lock the metal tube into position. Rolling over the interior tube is accomplished by pushing the tube onto a heated forming pin against a stop. When the end of the tube hits the stop it rolls back on itself forming a radially extending member. Heating the tool facilitates the forming of the member. Swaging and the rollover member form mechanical lock occurs between the tubes. The rollover member helps resist the ductile metal tube from being pulled off the interior tube.

In sum, the invention relates to a swaged medical device assembly including a first tubing with a proximal end, a distal end, a length, and an outside diameter and a ductile metal tubing. The ductile metal tubing has a proximal end, a distal end, a length, a lumen, and a first outside diameter. The ductile metal tubing is disposed over at least a portion of the length of the first tubing. A portion of the length of the ductile metal tubing has a smaller second outside diameter displacing a portion of the first tubing and a mechanical bond is formed therebetween. The proximal end of the first tubing may extend proximal of the proximal end of the ductile metal tubing and the proximal end of the first tubing may have at least one member extending in an outward radial direction from the longitudinal axis. The member provides one or more structural surfaces to cooperate with the ductile metal tubing and limit movement therebetween.

At least one member may cooperate with the ductile metal tubing to resist torque and tensile forces. The assembly may withstand a tensile force of less than about 8 pounds. The first tubing may be made of PEEK or PELLETHANE. The first tubing may have one or more lumens. The assembly may further include one or more additional elements of a stent delivery device. The first tubing may be a medical grade tubing. The assembly may be used in an implantable device or a medical device. The smaller second outside diameter have a length ranging from about one-half inch to about one and one-half inches. The assembly may cooperate with a valve body during stent deployment and reconstrainment. The ductile metal tubing may be made of a stainless steel. The stainless steel may be AISI 304. The stainless steel may be austenitic. The ductile metal tubing may be made of a carbon steel having a maximum Rockwell hardness of about 85B. The mechanical bond may be at least partially formed by resistance to displacement of the first tubing after a portion of the ductile metal tubing is reduced in diameter and contacts the first tubing. The ductile metal tubing may deform in a substantially radially inward direction for a distance sufficient to allow contact and mechanical bonding between the first tube and the ductile metal tubing. The assembly may be used as a handle.

The invention also relates to a method of forming a swaged medical device assembly including providing a first tubing made of a first material. The tubing has a proximal end, distal end, a first diameter, and an outside surface. A portion of the tubing is disposed in a ductile metal tubing; providing the ductile metal tubing having an outside surface, inside surface, a proximal end, a distal end, an interior lumen, a length, and a second diameter over at least a portion of the length; disposing the ductile metal tubing over at least a portion of the first tubing; applying force in a radially inward direction to at least a portion of the outside surface of the ductile metal tubing to reduce at least a portion of the second diameter to a smaller third diameter causing pressure to be transferred to the first tubing whereby a mechanical bond is formed between the ductile metal tubing and the first tubing. The method may further include providing a machine having preshaped dies adapted to apply one or more radial inward forces to a portion of the outside surface of the ductile metal tubing, the forces adapted to produce the smaller third diameter of a size sufficient to contact the first tubing and form a mechanical bond therebetween. The die may be a single taper, double taper, single extension, or double extension design. The method may further include inserting a mandrel into the first tubing prior to applying force in the radial inward direction. Reducing the outer diameter in the ductile metal tubing also may provide a substantially corresponding reduction in the inside diameter of the ductile metal tubing. The mechanical bond may include contact and resulting opposing forces between the first tubing and the ductile metal tubing. The method may further include rolling over an end of the first tubing. Rolling over the first tube may include pushing the tube over a heated mandrel against a stop and the proximal end of the first tube rolls in a distal direction to a position adjacent the swaged stainless steel tube.

The invention also relates to a method of using a swaged medical device assembly including providing a swaged tubing assembly comprising two or more components including a ductile metal tubing and second member mechanically bonded together, the assembly having proximal and distal portions; disposing the distal portion of the assembly into a body at a first site; pushing the swaged tubing assembly through one or more body vessels to a treatment site; performing a treatment or procedure; and withdrawing the swaged tubing assembly from the treatment site and body vessel.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawings and description are to be regarded as illustrative in nature, and not as restrictive.

DETAILED DESCRIPTION OF THE INVENTION

Figure 1:
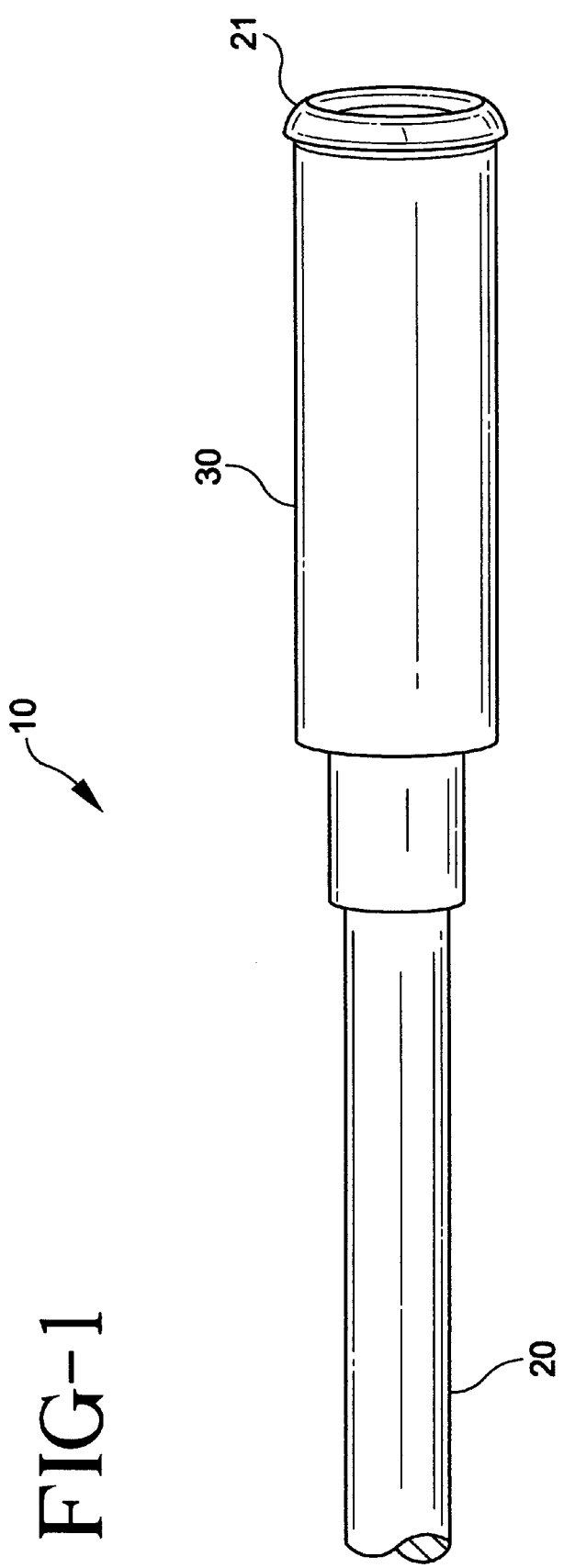
FIG. 1 is a schematic view of a handle assembly embodying the present invention.

Reference is made to FIG. 1 illustrating a ductile metal sleeve 30 such as stainless steel disposed and swaged on a tube 20. The swaging of the sleeve 30 onto the tubing 20 forms a connected assembly 10 which advantageously eliminates adhesives between the tubing 20 and sleeve 30 and generally provides a superior mechanical bond between the components. Prior to swaging, the sleeve 30 has a constant diameter and a center lumen with an inside diameter larger than the outside diameter of the tubing 20 which allows the tubing 20 to be removably disposed in the sleeve 30. After swaging, a portion of the sleeve 30 is locked onto the tubing 20 and forms the assembly 10. In the present invention, the reduction in outside diameter of the ductile metal tube from the original outside diameter to the swaged outside diameter may represent a diameter reduction in the range of about 2% to about 15%. A similar reduction of about 2% to about 15% in the inside diameter of the ductile metal tube also occurs.

Figure 2:
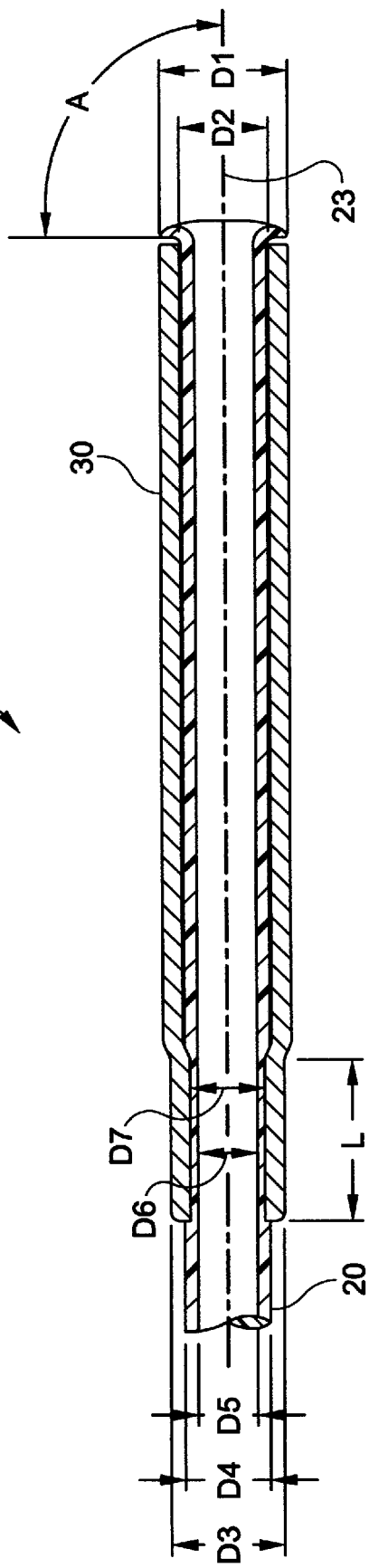
FIG. 2 is a cross-sectional side view of the handle assembly.

FIG. 2 illustrates a cross-sectional view of a preferred embodiment of the swaged assembly 10 and shows an exaggerated view of the deformation that occurs along about length L between the components 20, 30. In a preferred embodiment, prior to swaging, the outside diameter D1 of the sleeve 30 for 7 French to 10 French devices may range from about 0.065 inches to about 0.079 inches and the inside diameter D2 of the sleeve 30 may range from about 0.051 inches to about 0.065 inches. After swaging, the outside diameter D3 of the sleeve 30 over the swaged portion L may range from about 0.061 inches to about 0.075 inches. Prior to swaging, the outside diameter D4 of the tubing 20 may range from about 0.047 inches to about 0.061 inches. After swaging, the outside diameter D7 of the tubing 20 and the inside diameter of the sleeve 30, over the swaged length L, may range from about 0.043 inches to about 0.057 inches. Prior to swaging, the inside diameter D5 of the tubing 20 may range from about 0.020 inches to about 0.039 inches. After swaging, the inside diameter D6 of the tubing 20 over the swaged length L may range from about 0.020 inches to about 0.039 inches. The length L of the swaged area on sleeve 30 may range from about 0.5 inches to about 1.5 inches. Additional ranges for 11 French to 15 French devices are listed in Table 2. Other component and assembly sizes are also envisioned.

Table 1 below provides typical dimensions of a preferred embodiment of the assembly 10 for devices in about the 7 French to 10 French size range. However, other various sized components and assemblies are possible which incorporate the present invention.

Other catheter systems or delivery device systems up to 30 French size may advantageously incorporate the assembly of the present invention and use the method of joining metal and other members when it is desired to eliminate adhesives. In this example, the assembly serves as part of a handle for the catheter. The assembly may also be used as part of the catheter and as a way of adding stiffness and pushability to the catheter. Hypo tubes or other metal tubing may be joined to the inner member by the swaging method.

The proximal end 20A of the tubing 20 may have a rolled over member 21 flared in a radially outward direction in

TABLE 1

| Dimensions | First Tubing (Prior to Swaging) Range (Preferred (Inches) | First Tubing (After Swaging) Range/Preferred (Inches) | Ductile Metal Tubing (Prior to Swaging) Range/Preferred (Inches) | Ductile Metal Tubing (After Swaging) Range/Preferred (Inches) |
|---|---|---|---|---|
| D1 | N/A | N/A | .065–.079 .070 | .065–.079 .070 |
| D2 | N/A | N/A | .051–.065 .056 | .051–.065 .056 |
| D3 | N/A | N/A | N/A | .061–.075 .066 |
| D4 | .047–.061 .052 | .047–.061 .052 | N/A | N/A |
| D5 | .020–.039 .039 | .020–.039 .039 | N/A | N/A |
| D6 | .020–.039 .039 | .020–.039 .039 | N/A | N/A |
| D7 | N/A | .043–.057 .048 | N/A | N/A |
| Length L | N/A | .5–1.5 1 | N/A | .5–1.5 1 |
| Angle A | N/A | 5°–175° 45°–135° 90° | N/A | N/A |

Table 2 below provides typical dimensions of a preferred embodiment of the assembly 10 for devices in about the 11 French to 15 French size range. The preferred dimensions listed below reference a 11 French size assembly.

order to provide additional support and provide a second locking mechanism to limit movement of the tubing 20 and the sleeve 30. The angle A of the member 21 extending from the longitudinal axis 23 of the tubing 20 may range from

TABLE 2

| Dimensions | First Tubing (Prior to Swaging) Range (Preferred (Inches) | First Tubing (After Swaging) Range/Preferred (Inches) | Ductile Metal Tubing (Prior to Swaging) Range/Preferred (Inches) | Ductile Metal Tubing (After Swaging) Range/Preferred (Inches) |
|---|---|---|---|---|
| D1 | N/A | N/A | .079–.111 .106 | .079–.111 .106 |
| D2 | N/A | N/A | .067–.097 .085 | .067–.097 .085 |
| D3 | N/A | N/A | N/A | .071–.103 .094 |
| D4 | .063–.093 .084 | .063–.093 .084 | N/A | N/A |
| D5 | .020–.039 .039 | .020–.039 .039 | N/A | N/A |
| D6 | .020–.039 .039 | .020–.039 .039 | N/A | N/A |
| D7 | N/A | .057–.089 .080 | N/A | N/A |
| Length L | N/A | .5–1.5 1 | N/A | 5–1.5 1 |
| Angle A | N/A | 5°–175° 45°–135° 90° | N/A | N/A | about 5° to about 175°, preferably in the range of 45° to about 135°, and especially preferred about 90°.

Figure 3:
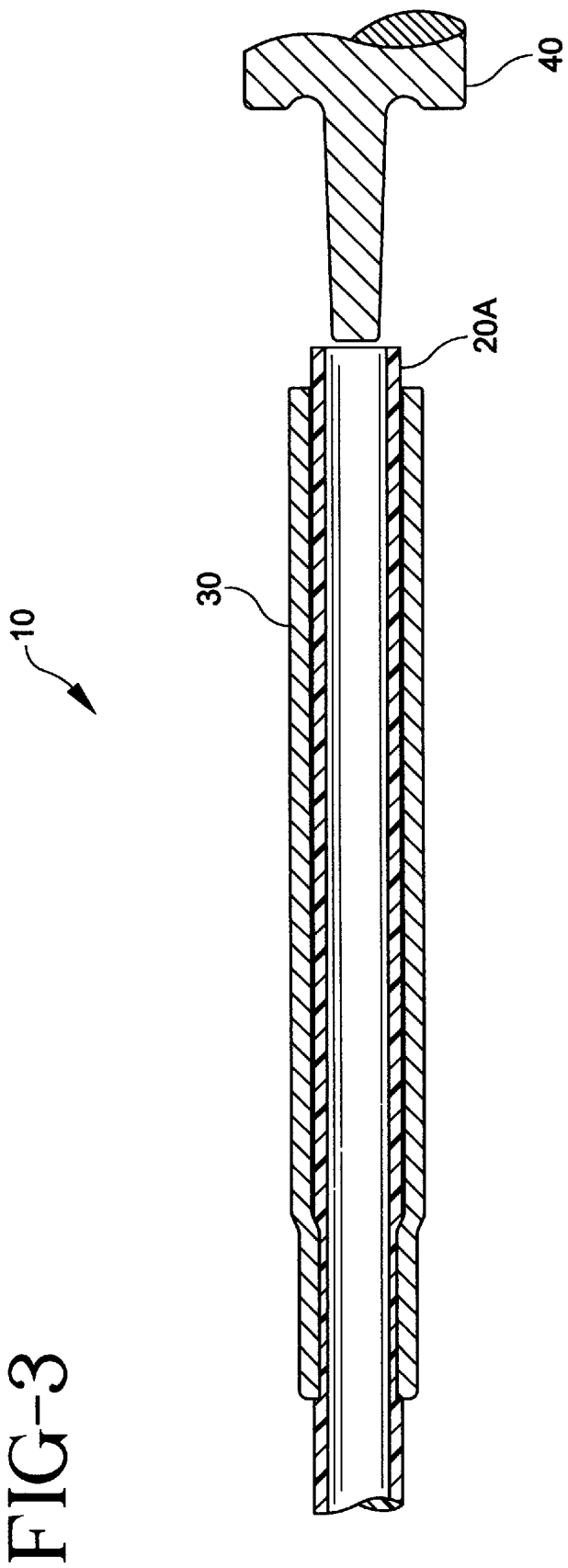
FIG. 3 is a side view of a die approaching an end of the handle assembly of FIG. 2 to form a rollover member.
Figure 4:
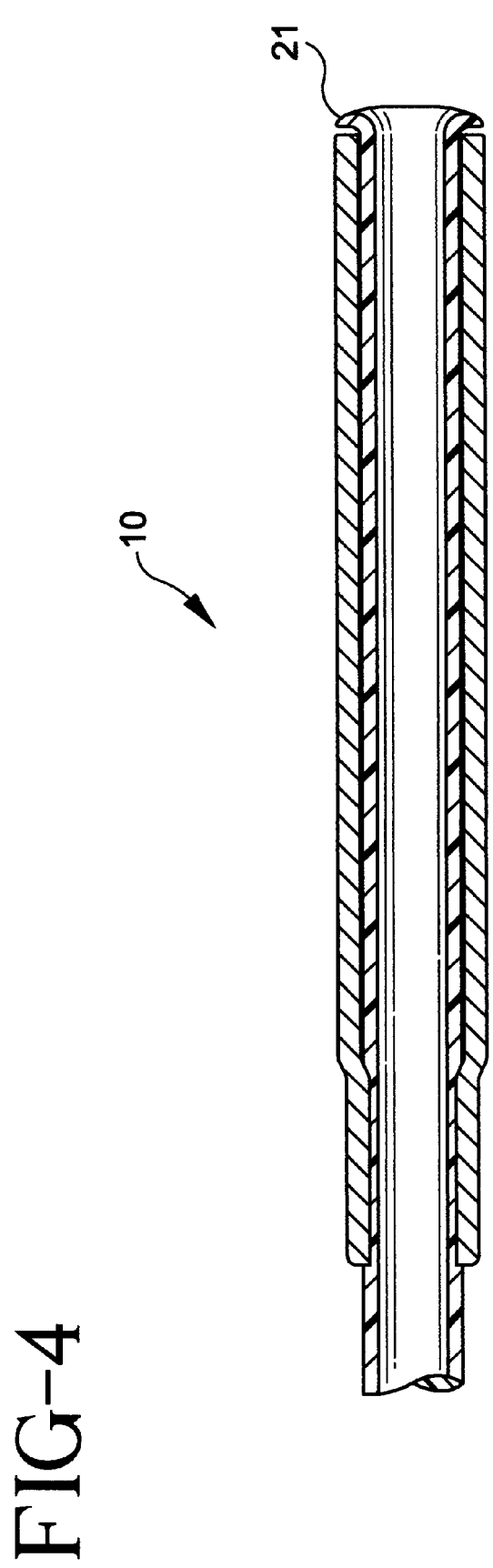
FIG. 4 is a side view of the assembly with the rollover member.

FIGS. 3 and 4 illustrate the heated mandrel or die 40 approaching the assembly 10. Rolling over the end of interior tube 20 to form a rollover member 21 involves pushing the tube 20 against a heated mandrel 40 and against a stop. As the heated mandrel 40 strikes the end of the tubing 20, the proximal end of the tubing 20 rolls over onto or against the end 20A of the ductile metal tubing 30 forming a rollover member 21 which provides an additional locking mechanism to secure the components 20, 30.

Although the present invention has been described with reference to preferred embodiments, those skilled in the art will recognize that changes can be made in form and detail without departing from the spirit and scope of the invention.

It will be evident from considerations of the foregoing that the Medical Device Tubing Assembly may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A method of forming a swaged medical device assembly comprising: providing a first tubing made of a first material, the tubing having a proximal end, a distal end, a first diameter, one or more lumens therethrough, and an outside surface, a portion of the tubing adapted to be disposed in a ductile metal tubing;

providing the ductile metal tubing having an outside surface, an inside surface, a proximal end, a distal end, an interior lumen, a length, and a second diameter over at least a portion of the length;

providing at least one mandrel dimensioned to fit within the one or more lumens of the first tubing;

disposing the at least one mandrel in the one or more lumens of the first tubing;

disposing the metal tubing over at least a portion of the first tubing;

applying force in a radially inward direction to at least a portion of the outside surface of the ductile metal tubing to reduce at least a portion of the second diameter to a smaller third diameter causing pressure to be transferred to the first tubing whereby a mechanical bond is formed between the ductile metal tubing and the first tubing;

rolling over an end of the first tubing wherein rolling over the first tube includes pushing the tube over a heated mandrel against a stop whereby the proximal end of the first tube rolls in a distal direction to a position adjacent the swaged stainless steel tube; and removing the at least one mandrel from the one or more lumens such that the one or more lumens are maintained and the mechanical bond between the ductile metal tubing and the first tubing is preserved.

* * * * *